United States Patent [19]
Phillips et al.

[11] Patent Number: 4,734,209
[45] Date of Patent: Mar. 29, 1988

[54] METAL DEACTIVATORS

[75] Inventors: Emyr Phillips, Sale; Brian Holt, Stretford, both of England

[73] Assignee: Ciba-Geigy Corporation, Ardsley, N.Y.

[21] Appl. No.: 718,907

[22] Filed: Apr. 2, 1985

[30] Foreign Application Priority Data

Apr. 4, 1984 [GB] United Kingdom ............... 8408617

[51] Int. Cl.$^4$ .................................... C10M 133/42
[52] U.S. Cl. .................................. 252/47; 252/47.5; 252/50; 252/51.5 R; 72/42
[58] Field of Search ................. 252/50, 51.5 R, 47, 252/47.5; 548/262, 266; 72/42

[56] References Cited

U.S. PATENT DOCUMENTS

| | | | |
|---|---|---|---|
| 3,647,814 | 3/1972 | Greenfield | 548/262 |
| 3,663,436 | 5/1972 | Carswell | 252/50 |
| 3,914,179 | 10/1975 | Byford et al. | 252/50 |
| 4,278,553 | 7/1981 | Sunz et al. | 252/50 |
| 4,392,968 | 7/1983 | Ishida et al. | 252/50 |

FOREIGN PATENT DOCUMENTS 0052393  3/1983  Japan ................................ 252/50

Primary Examiner—Jacqueline V. Howard
Attorney, Agent, or Firm—Edward McC. Roberts; Kevin T. Mansfield

[57] ABSTRACT

New N-substituted compounds, useful as metal deactivators in functional fluids, have the formula I:

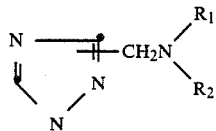

in which $R_1$ and $R_2$ are the same or different and each is $C-C_{20}$ alkyl, $C_3-C_{20}$ alkenyl, $C_5-C_{12}$ cycloalkyl, $C_7-C_{13}$ aralkyl, $C_6-C_{10}$ aryl, or $R_1$ and $R_2$, together with the nitrogen atom to which they are each attached form a 5-, 6- or 7-membered heterocyclic residue, or $R_1$ and $R_2$ is each a residue of formula II:

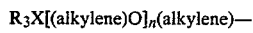

in which X is O, S or N, $R_3$ is hydrogen or $C_1$–$C_{20}$ alkyl, alkylene is a $C_1$–$C_{12}$ alkylene residue and n is 0 or an integer from 1 to 6, or $R_1$ has its previous significance and $R_2$ is a residue of formula III:

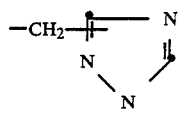

or $R_2$ is a residue of formula III as defined above $R_1$ is a residue of formula IV:

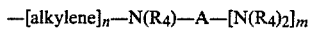

wherein m is zero or 1 and, when m is zero, A is a residue of formula III and, when m is 1, A is alkylene or $C_6$–$C_{10}$- arylene and alkylene and n have their previous significance and $R_4$ is a residue of formula III, as hereinbefore defined.

3 Claims, No Drawings

METAL DEACTIVATORS

The present invention relates to new metal deactivators, in particular to new triazole derivatives useful as metal deactivators in functional fluids.

The present invention provides new N-substituted compounds having the formula I

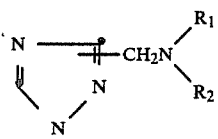

in which $R_1$ and $R_2$ are the same or different and each is $C_1$–$C_{20}$ alkyl, $C_3$–$C_{20}$ alkenyl, $C_5$–$C_{12}$ cycloalkyl, $C_7$–$C_{13}$ aralkyl, $C_6$–$C_{10}$ aryl, or $R_1$ and $R_2$, together with the nitrogen atom to which they are each attached may form a 5-, 6- or 7-membered heterocylic residue, or $R_1$ and $R_2$ is each a residue of formula II:

$$R_3X[(alkylene)O]_n(alkylene)—$$ II in which X is O, S or N, $R_3$ is hydrogen or $C_1$–$C_{20}$ alkyl, "alkylene" is a $C_1$–$C_{12}$ preferably $C_1$–$C_6$ especially $C_2$–$C_3$ alkylene residue and n is 0 or an integer from 1 to 6, preferably 0, 1, 2, 3 or 4; or $R_1$ has its previous significance and $R_2$ is a residue of formula III

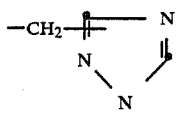

or $R_2$ is a residue of formula III as defined above and $R_1$ is a residue of formula IV:

$$—[alkylene]_n—N(R_4)—A—[N(R_4)_2]_m$$ IV wherein m is zero or 1 and, when m is zero, A is a residue of formula III and, when m is 1, A is alkylene or $C_6$–$C_{10}$-arylene and alkylene and n have their previous significance and $R_4$ is a residue of formula III, as hereinbefore defined.

When the group $R_1$ and/or $R_2$ and/or $R_3$ is a $C_1$–$C_{20}$ alkyl group it may be straight- or branched chain and may be e.g. methyl, ethyl, n-propyl, iso-propyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl or n-eicosyl.

When the group $R_1$ and/or $R_2$ is a $C_3$–$C_{20}$ alkenyl group, it may be straight- or branched chain and may be e.g. prop-2-enyl, but-2-enyl, 2-methyl-prop-2-enyl, pent-2-enyl, hexa-2,4-dienyl, dec-10-enyl or eicos-2-enyl.

$C_5$–$C_{12}$ cylcoalkyl groups $R_1$ and/or $R_2$ may be cyclopentyl, cyclohexyl, cyclooctyl, cyclodecyl, adamantyl or cyclododecyl.

$C_7$–$C_{13}$ aralkyl groups $R_1$ and/or $R_2$ are e.g. benzyl, 2-phenylethyl, benzhydryl or naphthylmethyl.

$C_6$- or $C_{10}$ aryl groups $R_1$ and/or $R_2$ are e.g. phenyl or naphthyl.

When $R_1$ and $R_2$ together with the nitrogen atom to which they are attached form a heterocyclic residue it may be a morpholine, pyrrolidine, piperidine or perhydroazepine residue.

$C_1$–$C_{12}$ alkylene moieties in the residue of formula (II) or IV include methylene, ethylene, 1:2- or 1:3-propylene, 1:4-butylene, 1:6-hexylene, 1:8-octylene, 1:10-decylene and 1:12-dodecylene groups.

$C_6$–$C_{10}$ Arylene moieties in the residue IV include phenylene and naphthylene groups.

Specific compounds of formula I include:
1-(or 4)-(dimethylaminomethyl) triazole
1-(or 4)-(diethylaminomethyl) triazole
1-(or 4)-(di-isopropylaminomethyl) triazole
1-(or 4)-(di-n-butylaminomethyl) triazole
1-(or 4)-(di-n-hexylaminomethyl) triazole
1-(or 4)-(di-n-octylaminomethyl) triazole
1-(or 4)-(di-n-decylaminomethyl) triazole
1-(or 4)-(di-n-dodecylaminomethyl) triazole
1-(or 4)-(di-n-octadecylaminomethyl) triazole
1-(or 4)-(di-n-eicosylaminomethyl) triazole
1-(or 4)-[di-(prop-2'-enyl)aminomethyl] triazole
1-(or 4)-[di-(but-2'-enyl)aminomethyl] triazole
1-(or 4)-[di-(eicos-2'-enyl)aminomethyl] triazole
1-(or 4)-(di-cyclohexylaminomethyl) triazole
1-(or 4)-(di-benzylaminomethyl) triazole
1-(or 4)-(di-phenylaminomethyl) triazole
1-(or 4)-(4'-morpholinomethyl) triazole
1-(or 4)-(1'-pyrrolidinomethyl) triazole
1-(or 4)-(1'-piperidinomethyl) triazole
1-(or 4)-(1'-perhydoroazepinomethyl) triazole
1-(or 4)-(2',2''-dihydroxyethyl)aminomethyl] triazole
1-(or 4)-(dibutoxypropyl-aminomethyl) triazole
1-(or 4)-(dibutylthiopropyl-aminomethyl) triazole
1-(or 4)-(di-butylaminopropyl-aminomethyl) triazole
N,N-bis-(1- or 4-triazolylmethyl) laurylamine
N,N-bis-(1- or 4-triazolylmethyl) oleylamine
N,N-bis-(1- or 4-triazolylmethyl) ethanolamine
N,N,N',N'-tetra(1- or 4 -triazolylmethyl) ethylene diamine.

The present invention also provides a process for producing compounds of formula I comprising reacting a compound having the formula V:

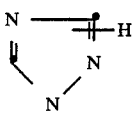

with formaldehyde and with an amine having the formula VI:

$$HNR_1R_2$$ VI wherein $R_1$ and $R_2$ have their previous significance.

The formaldehyde reactant is conveniently used as formalin or paraformaldehyde.

The relative proportions of the reactants of formula V and VI and of formaldehyde used will vary depending on whether the amine of formula VI is a primary or secondary amine or a di-, tri- or tetra-amine. When the amine of formula VI is a primary amine, the molar ratios used of compound of formula V: formaldehyde: amine VI are preferably substantially 2:2:1 or 1:1:1; when the amine VI is a secondary amine, the molar ratios used are preferably substantially 1:1:1; and when the amine VI is a diamine, the molar ratios used are preferably 4:4:1.

The process of the present invention is conveniently effected by heating all the reactants together at an elevated temperature, preferably at a temperature within the range of from 50° to 120° C., optionally in the presence of an inert solvent such as water, a $C_1$–$C_4$ alkanol, a petroleum solvent e.g. hexane, isooctane or cyclohexane or an aromatic solvent such as benzene, toluene or a xylene.

Alternatively, compound V may be reacted first with formaldehyde to give the N-methylol compound, which can then be reacted with the amine of formula VI.

As a further alternative, the compound of formula V may be reacted with the corresponding amine methylol compound.

The new compounds of formula I have valuable properties as metal deactivators in functional fluids and as foam inhibitors in printing inks for use in the production of textured foamed resin materials (as described in U.S. Pat. No. 4,407,882).

Accordingly, the present invention also provides a composition comprising a functional fluid and, as metal deactivator, a metal deactivating proportion, preferably 0.001% to 5% by weight, on total composition, of a compound of formula I as hereinabove defined.

Examples of functional fluids useful as substrates for the compositions of the invention are lubricants having a mineral oil, poly-alpha olefin or synthetic carboxylic ester base; hydraulic fluids based on mineral oils, phosphate esters, aqueous polyglycol/polyglycol ether mixtures, glycol systems; oil-in-water or other water-in-oil emulsions; metal-working fluids having, as their base, mineral oil or aqueous systems; aqueous or aqueous glycol or ethylene- or propylene glycol/methanol based engine coolant compositions; and transformer and switch oils.

Examples of synthetic lubricants include lubricants based on a diester of a dibasic acid and a monohydric alcohol, for instance dioctyl sebacate or dinonyl adipate; on a triester of trimethylol propane and a monobasic acid or mixture of such acids, for instance trimethylol propane tripelargonate, trimethylol propane tricaprylate or mixtures thereof; on a tetraester of pentaerythritol and a monobasic acid or mixture of such acids, for instance pentaerythritol tetracaprylate; or on complex esters derived from monobasic acids, dibasic acids and polyhydric alcohols, for instance a complex ester derived from trimethylol propane, caprylic acid and sebacic acid; or of mixtures thereof.

Other synthetic lubricants are those known to the art-skilled and described e.g. in "Schmiermittel-Taschenbuch" (Huethig Verlag, Heidelberg 1974). Especially suitable, apart from the preferred mineral oils are e.g. phosphates, glycols, polyglycols, polyalkylene glycols and poly-alpha olefins.

Of particular interest are aqueous-based functional fluids e.g. anti-freezes, and hydraulic- and metal-working fluids. For use in this type of aqueous-based fluid, those compounds of formula I are preferred in which $R_1$ and/or $R_2$ is a hydrophilic residue of formula II.

On the other hand, for use in oil-based functional fluids, compounds of formula I are preferred in which $R_1$ and/or $R_2$ is an oleophilic group.

In order to improve various applicational properties, the compositions of the invention may also contain other additives such as, for oil-based systems, one or more of antioxidants, other metal deactivators, rust inhibitors, viscosity-index improvers, pour-point depressants, dispersants/surfactants or anti-wear additives; and for aqueous-based systems, one or more of antioxidants, corrosion- and rust inhibitors, further metal deactivators, extreme pressure- or anti-wear additives, complexing agents, precipitation inhibitors, biocides, buffering agents and anti-foams.

For oil-based systems, examples of other additives are:

Examples of phenolic antioxidants

1. Alkylated monophenols 2,6-di-tert.butylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 2. Alkylated hydroquinones 2,6-di-tert.butyl-4-methoxyphenol
2,5-di-tert.butyl-hydroquinone
2,5-di-tert.amyl-hydroquinone
2,6-diphenyl-4-octadecyloxyphenol 3. Hydroxylated thiodiphenyl ethers 2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

4. Alkyliden-bisphenols 2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
2,2'-methylene-bis-[6-(α-methylbenzyl)-4-nonylphenol]
2,2'-methylene-bis-[6-(α,α-dimethylbenzyl)-4-nonylphenol]
4,4'-methylene-bis-(6-tert.butyl-2-methylphenol)
1,1-bis-(5-tert.butyl-4-hydroxy-2-methylphenyl)-butane
2,6-di-(3-tert.butyl-5-methyl-2-hydroxybenzyl)-4-methylphenol
1,1,3-tris-(5-tert.butyl-4-hydroxy-2-methylphenyl)-3-n-dodecylmercapto butane
ethylenglycol-bis-[3,3-bis-(3'-tert.butyl-4'-hydroxyphenyl)-butyrat]
di-(3-tert.butyl-4-hydroxy-5-methylphenyl)-dicyclopentadien
di-[3'-tert.butyl-2'-hydroxy-5'-methyl-benzyl)-6-tert.butyl-4-methylphenyl]-terephthalate.

5. Benzylcompounds 1,3,5-tri-(3,5-di-tert.butyl-4-hydroxybenzyl)-2,4,6-trimethylbenzene
di-(3,5-di-tert.butyl-4-hydroxybenzyl)-sulfide
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphonic acid-dioctadecyl ester 3,5-di-tert.butyl-4-hydroxybenzyl-phosphonic acid-monoethyl ester, calcium-salt 6. Acylaminophenols 4-hydroxy-lauric acid anilide
4-hydroxy-stearic acid anilide 2,4-bis-octylmercapto-6-(3,5-di-tert.butyl-4-hydrox-
  yanilino)-s-triazine
N-(3,5-di-tert.butyl-4-hydroxyphenyl)-carbamic acid
  octyl ester 7. Esters of β-(3,5-di-tert.butyl-4-hydroxyphenyl)-propionic acid with monohydric or polyhydric alcohols e.g. with
methanol
diethyleneglycol
octadecanol
triethyleneglycol
1,6-hexanediol
pentaerythritol
neopentylglycol
tris-hydroxyethyl isocyanurate
thiodiethyleneglycol
di-hydroxyethyl oxalic acid diamide 8. Esters of β-(5-tert.butyl-4-hydroxy-3-methyl-phenyl)propionic acid with monohydric or polyhydric alcohols e.g. with
methanol
diethyleneglycol
octadecanol
triethyleneglycol
1,6-hexanediol
pentaerytritol
neopentylglycol
tris-hydroxyethyl isocyanurate
thiodiethyleneglycol
di-hydroxyethyl oxalic acid diamide 9. Amides of β-(3,5-di-tert.butyl-4-hydroxyphenyl)-propionic acid e.g.
N,N'-di-(3,5-di-tert.butyl-4-hydroxyphenylpropionyl)-
  hexamethylendiamine
N,N'-di-(3,5-di-tert.butyl-4-hydroxyphenylpropionyl)-
  trimethylendiamine
N,N'-di-(3,5-di-tert.butyl-4-hydroxyphenylpropionyl)-
  hydrazine Examples of amine antioxidants N,N'-di-isopropyl-p-phenylenediamine
N,N'-di-sec.-butyl-p-phenylenediamine
N,N'-bis(1,4-dimethyl-pentyl)-p-phenylenediamine
N,N'-bis(1-ethyl-3-methyl-pentyl)-p-phenylenediamine
N,N'-bis(1-methyl-heptyl)-p-phenylenediamine
N,N'-dicyclohexyl-p-phenylenediamine
N,N'-diphenyl-p-phenylenediamine
N,N'-di-(naphtyl-2-)-p-phenylenediamine
N-isopropyl-N'-phenyl-p-phenylenediamine
N-(1,3-dimethyl-butyl)-N'-phenyl-p-phenylenediamine
N-(1-methyl-heptyl)-N'-phenyl-p-phenylenediamine
N-Cyclohexyl-N'-phenyl-p-phenylenediamine
4-(p-toluol-sulfonamido)-diphenylamine
N,N'-dimethyl-N,N'-di-sec.-butyl-p-phenylenediamine
  diphenylamine
4-isopropoxy-diphenylamine
N-phenyl-1-naphthylamine
N-Phenyl-2-naphthylamine
octylated diphenylamine
octylated N-phenyl-α(or β) naphthylamine
4-butylamino-phenol
4-butyrylamino-phenol
4-nonanoylamino-phenol
4-dodecanoyl-p-amino-phenol
4-octadecanoyllamino-phenol
Di-(4-methoxy-phenyl)-amine
2,6-di-tert.-butyl-4-dimethylamino-methyl-phenol
2,4'-diamino-diphenylmethane
4,4'-diamino-diphenylmethane
N,N,N',N'-tetramethyl-4,4'-diamino-phenylmethane
1,2-di-(phenylamino)-ethane
1,2-di-[(2-methyl-phenyl)-amino]-ethane
1,3-di-(phenylamino)-propane
(o-tolyl)-biguanide
di-[4-(1',3'-dimethyl-butyl)-phenyl]amine Examples of metal passivators are:

for copper e.g.
Benzotriazole, tolutriazole and derivatives thereof, tetrahydrobenzotriazole, 2-mercaptobenzthiazole, 2,5-dimercaptothiadiazole, salicylidene-propylenediamine, salts of salicylaminoguanidine.

Examples of rust inhibitors are:

(a) Organic acids, their esters, metal salts and anhydrides e.g. N-oleyl-sarcosine, sorbitan-mono-oleate, lead-naphthenate, dodecenyl-succinic acid (and its partial esters and amides), 4-nonyl-phenoxy-acetic acid.
(b) Nitrogen-containing compounds e.g.
  I. Primary, secondary or tertiary aliphatic or cycloaliphatic amines and amine-salts of organic and inorganic acides e.g. oils-soluble alkylammonium carboxylates
  II. Heterocyclic compounds e.g. substituted imidazolines and oxazolines
(c) Phosphorous-containing compounds e.g. Amine salts of phosphonic acid partial esters, zinc dialkyl-dithio phosphates
(d) Sulfur-containing compounds e.g. Barium-dinonyl-naphthalene-n-sulfonates, calcium petroleum sulfonates Examples of viscosity-index improvers are e.g.

Polymethacrylates, vinylpyrrolidone/methacrylate-copolymers, polybutenes, olefin-copolymers, styrene/acrylate-copolymers.

Examples of pour-point depressants are e.g.

Polymethacrylates, or alkylated naphthalene derivatives

Examples of dispersants/surfactants are e.g.

Polybutenylsuccinic acid-amides, polybutenylphosphonic acid derivatives, basic magnesium-, calcium-, and bariumsulfonates and -phenolates.

Examples of anti-wear additives are e.g.

Sulfur- and/or phosphorus- and/or halogen-containing compounds e.g. sulfurised vegetable oils, zinc dialkyl-dithiophosphates, Tritolyl-phospate, chlorinated paraffins, alkyl- and aryldisulfides.

for aqueous-based systems, examples of antioxidants etc are listed hereinbefore in relation to oil-based systems and which are water-soluble.

Examples of buffering agents are borax and triethanolamine; examples of biocides are 2,4,5-trichlorophenol; and the sodium salts of 2,2'-dihydroxy-5,5'-dichlorodiphenylmethane and orthophenylphenol, respectively; and examples of antifoams are silicones.

The new compounds of formula I combine excellent metal deactivation properties with good solubility in both oil- and water-based functional fluids, respectively. Moreover, they do not form insoluble salts when used together with anti-wear additives containing zinc, e.g. zinc dialkyldithiophosphates.

The following Examples further illustrate the present invention. All parts and percentages given therein are by weight.

EXAMPLE 1

3,5 parts of triazole and 12.05 parts of di-2-ethylhexylamine are mixed with 100 parts of methanol, and 4.05 parts of 36% aqueous formalin are added. The mixture is heated, under reflux, for 3 hours. The solvent is then removed under water pump vacuum. In this way 1-di-2-ethylhexylaminomethyltriazole is obtained in 100% theory yield, with a boiling point of 189° C. at 0.07 m bar.

EXAMPLE 2

7 parts of triazole and 12.9 parts of di-n-butylamine and 8.1 parts of 37% aqueous formaldehyde mixed with 100 parts of methanol, are reacted as in Example 1 to provide 20.4 parts (97% yield) 1-di-n-butylaminomethyltriazole. Boiling point 105° C./0.075 m bar.

EXAMPLE 3

13.8 parts of triazole, 26.8 parts of oleylamine and 16.2 parts of 37% aqueous formaldehyde mixed with 100 parts of methanol, are reacted as in Example 1 to provide 41.7 parts N,N-bis(1-triazolylmethyl)oleylamine, as a viscous oil.

EXAMPLE 4

10.5 parts of diethanolamine are added to a clear solution of 6.9 parts of triazole and 8.1 parts 36% aqueous formaldehyde in 100 parts water. The mixture is heated under reflux for 8 hours. The solvent is then removed under vacuum. In this way 1-[2,2'-dihydroxyethyl)aminomethyl] triazole is obtained in 95% yield. Boiling point 115° C./0.08 m bar.

EXAMPLE 5

A 0.05% solution of the product of Example 1 is prepared in a turbine quality mineral oil containing 50 ppm of added, dissolved sulphur.

A copper strip (60×10×1 mm) is polished with 100 grade silicon carbide grit which has been picked up on cotton wool wetted with petroleum ether. The polished strip is then immediately totally immersed in the prepared solution, which is maintained at 100° C. for 2 hours. After this time, the strip is removed, washed with petroleum ether, dried and its colour is compared with those of the ASTM D130 Copper Strip Corrosion Standard Chart. On this rating, 1 represents zero to slight tarnish; 2 represents moderate tarnish; 3 represents dark tarnish; and 4 represents corrosion; and the designations A, B and D indicate shadings within the numerical gradings.

The results are set out in the following Table I.

TABLE I

| Example | Metal Appearance/Rating | Solution Appearance |
| --- | --- | --- |
| control | Magenta - Rating 3B | colourless |
| 5 | No change - Rating 1A | colourless |

EXAMPLE 6

A 0.05% solution of the product of Example 4 is prepared in water containing 0.132 g/l MgSo$_4$.7H$_2$O and 0.68 g/l CaCl$_2$.6H$_2$O (water as used in DIN 51360 test), and the pH of the solution is adjusted to 7-8 with sodium hydroxide.

A piece of copper foil (20×50×0.1 mm) is cleaned by rubbing it with cotton wool soaked with water and powdered pumice, dried and weighed. It is then fully immersed in 50 ml of the solution so prepared contained in a 60 ml bottle fitted with a screw cap. The bottle is then placed for 24 hours in an oven maintained at 70° C. At the end of this time, the strip is removed, washed and dried and its colour is recorded (using the ASTM D130 colour ranking). It is then immersed for 15 seconds in 5N hydrochloric acid at 120° C., washed, dried and reweighed.

The results are summarised in Table II:

TABLE II

| Example | Weight loss (mg) | Metal Appearance and rating | Solution Appearance |
| --- | --- | --- | --- |
| control | 4.6 | purple-black rating 4D | colourless |
| 6 | 0.4 | no change rating 1A | colourless |

EXAMPLE 7

6.9 parts of triazole, 18.1 parts of dicyclohexylamine and 8.1 parts of 37% aqueous formaldehyde mixed with 100 parts of methanol are reacted as in Example 1 to provide 24 parts (92% yield) 1-N,N-dicyclohexylaminomethyltriazole. Melting point 62°-64° C.

EXAMPLE 8

A 0.05% solution of the product of Example 7 is prepared in a turbine quality mineral oil and tested as in Example 5.

The result is set out in Table III.

TABLE III

| Example | Metal Appearance/Rating | Solution Appearance |
| --- | --- | --- |
| control | Magenta - Rating 3B | colourless |
| 8 | No change - Rating 1A | colourless |

EXAMPLE 9

6.9 parts triazole, 9.7 parts diallylamine and 8.1 parts 37% aqueous formaldehyde mixed with 100 parts of methanol are reacted, as in Example 1, to provide 16.4 parts (89% yield) of 1-N,N-diallylaminomethyltriazole. Boiling point 140° C./0.2 m bar.

EXAMPLE 10

13.8 parts triazole, 9.3 parts aniline and 16.2 parts 37% aqueous formaldehyde mixed with 100 parts of methanol are reacted, as in Example 1, to provide 19.6 parts (78%) of N,N-bis(triazolyl-methylene)aniline as a viscous oil.

EXAMPLE 11

27.6 parts triazole, 6 parts diaminoethane and 32.4 parts 37% aqueous formaldehyde mixed with 100 parts of methanol are reacted, as in Example 1, to provide 37.3 parts (97% yield) of N,N,N',N'-tetra(triazolylmethylene)diaminoethane. Melting point 127°-129° C.

EXAMPLE 12

34.5 parts triazole, 10.3 parts diethylenetriamine and 40.5 parts 37% aqueous formaldehyde mixed with 100 parts of methanol are reacted, as in Example 1, to provide 44.2 parts (95% yield) N,N,N',N'',N''-penta(- triazolylmethylene)diethylenetriamine as a viscous orange oil.

What is claimed is:

1. A composition comprising a functional fluid and, as metal deactivator, a metal deactivating proportion of an N-substituted compound of the formula I

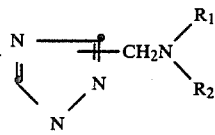   I in which $R_1$ and $R_2$ are the same or different and each is $C_1$–$C_{20}$ alkyl, $C_3$–$C_{20}$ alkenyl, $C_5$–$C_{12}$ cycloalkyl, $C_7$–$C_{13}$ aralkyl, $C_6$–$C_{10}$ aryl, or $R_1$ and $R_2$, together with the nitrogen atom to which they are each attached form a 5-, 6- or 7-membered heterocyclic residue, or $R_1$ and $R_2$ is each a residue of formula II:

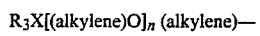   II in which X is O, S or N, $R_3$ is hydrogen or $C_1$–$C_{20}$ alkyl, "alkylene" is a $C_1$–$C_{12}$ alkylene residue and n is 0 or an integer from 1 to 6; or $R_1$ has its previous significance and $R_2$ is a residue of formula III:

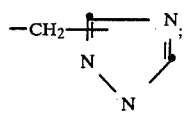   III or $R_2$ is a residue of formula III as defined above and $R_1$ is a resiude of formula IV:

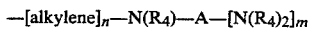   IV wherein m is zero or 1 and, when m is zero, A is a residue of formula III and, when m is 1, A is alkylene or $C_6$–$C_{10}$-arylene, and alkylene and n have their previous significance and $R_4$ is a residue of formula III, as hereinabove defined.

2. Composition according to claim 1 wherein the proportion of the compound of formula I is from 0.001 to 5% by weight, based on the weight of the total composition.

3. A composition according to claim 1 wherein, in the compound of formula I, $R_1$ and $R_2$ are both 2-ethylhexyl.

* * * * *